(12) United States Patent
Kikuiri

(10) Patent No.: US 8,231,840 B2
(45) Date of Patent: Jul. 31, 2012

(54) FECES COLLECTION CONTAINER

(75) Inventor: Hideki Kikuiri, Tsuyama (JP)

(73) Assignee: Alfresa Pharma Corporation (JP)

( * ) Notice: Subject to any disclaimer, the term of this patent is extended or adjusted under 35 U.S.C. 154(b) by 1269 days.

(21) Appl. No.: 11/631,432

(22) PCT Filed: Jun. 28, 2005

(86) PCT No.: PCT/JP2005/011833
§ 371 (c)(1),
(2), (4) Date: Jan. 3, 2007

(87) PCT Pub. No.: WO2006/006394
PCT Pub. Date: Jan. 19, 2006

(65) Prior Publication Data
US 2008/0034899 A1    Feb. 14, 2008

(30) Foreign Application Priority Data

Jul. 12, 2004 (JP) .................................. 2004-205150

(51) Int. Cl.
*G01N 33/52* (2006.01)
(52) U.S. Cl. ........ 422/411; 422/405; 422/406; 422/942; 436/810
(58) Field of Classification Search .................. 422/102, 422/202, 260, 301, 61, 58, 405, 406, 411, 422/942; 436/810, 809
See application file for complete search history.

(56) References Cited

U.S. PATENT DOCUMENTS

| 4,299,920 | A | * | 11/1981 | Peters | 435/288.4 |
| 4,409,988 | A | * | 10/1983 | Greenspan | 600/572 |
| 4,865,813 | A | * | 9/1989 | Leon | 422/101 |
| 5,514,341 | A | * | 5/1996 | Urata et al. | 422/102 |

FOREIGN PATENT DOCUMENTS

| EP | 1 366 715 A1 | 12/2003 |
| JP | 8-82622 | 3/1996 |
| JP | 08-292189 | 11/1996 |
| JP | 11-064331 | 3/1999 |
| JP | 2002-207033 | 7/2002 |
| JP | 2004-4014 | 1/2004 |

* cited by examiner

*Primary Examiner* — Michael Marcheschi
*Assistant Examiner* — Jonathan Hurst
(74) *Attorney, Agent, or Firm* — Gerald E. Hespos; Michael J. Porco

(57) ABSTRACT

A suspension storage container 10 has a flat portion across a specific region including the tail end. The flat portion has an outer peripheral wall 13 forming a flat outer peripheral surface and partition walls 14 that extend in the flat cross section of the outer peripheral wall 13 in a direction substantially orthogonal to the major axis direction of the flat cross section to partition a chamber inside the outer peripheral wall 13 into plural chambers S1 through S3 aligned side by side in the major axis direction. A suspension K is stored only in part of all the chambers S1 through S3, that is, the chamber S2, and a sealing film 21 having the outline almost identical with the outline of the outer peripheral wall is laminated to the tail end surfaces of the outer peripheral wall 13 and the partition walls 14.

14 Claims, 9 Drawing Sheets

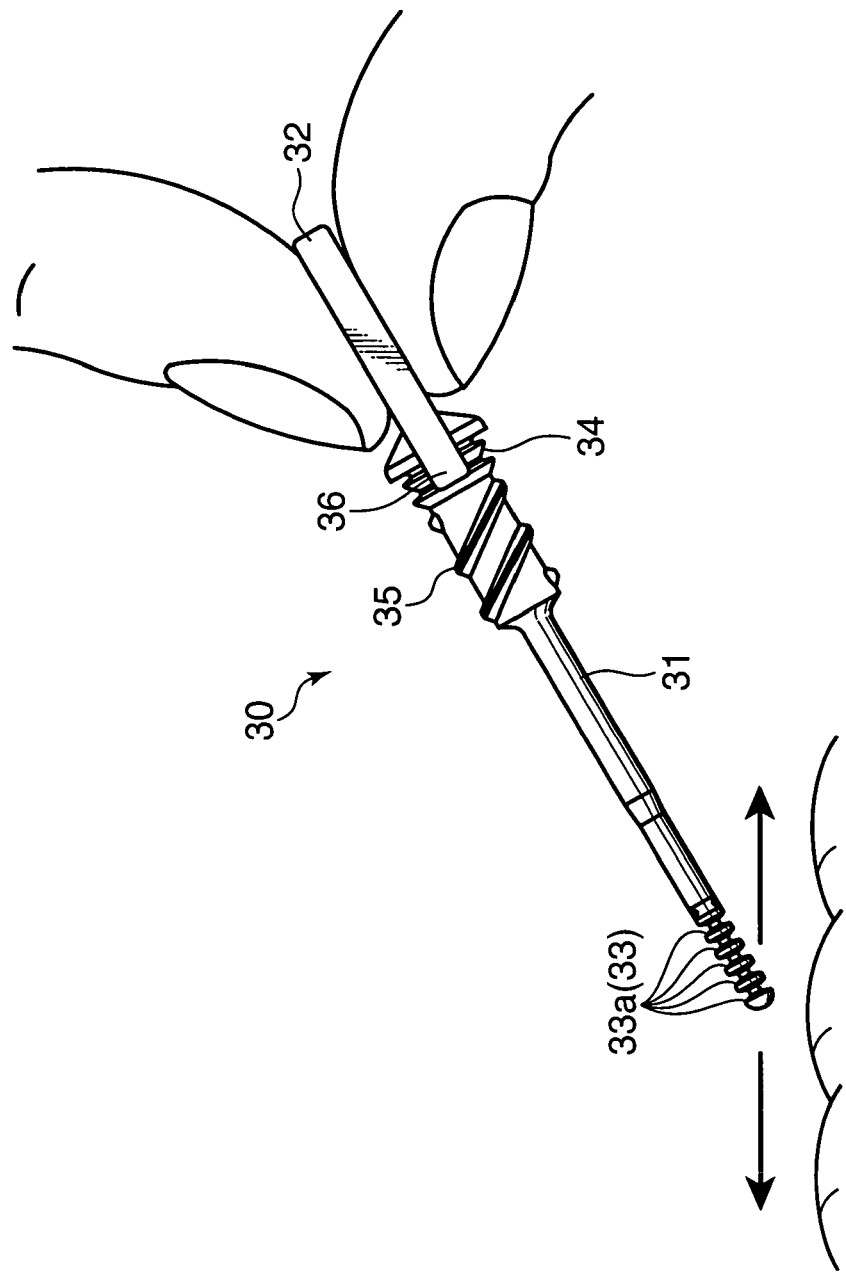

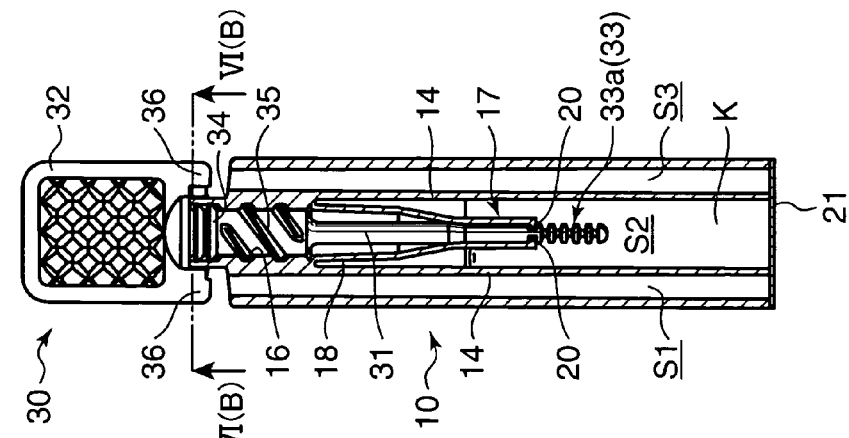
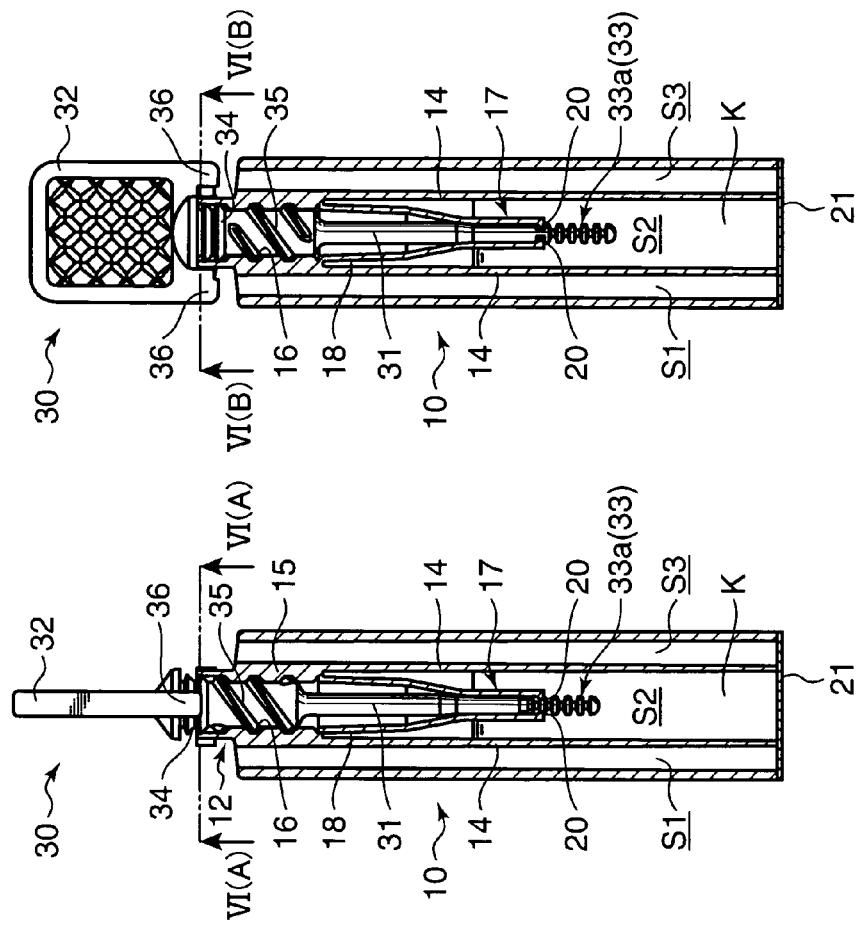
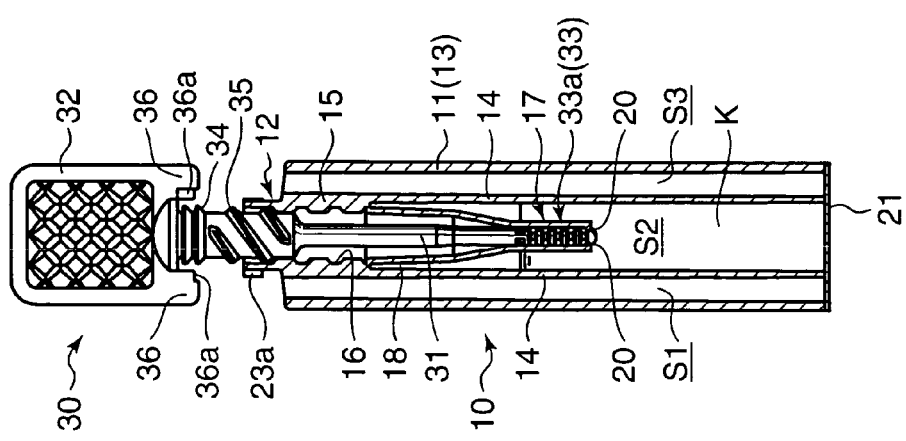

FECES COLLECTION CONTAINER

BACKGROUND OF THE INVENTION

1. Field of the Invention

The present invention relates to a feces collection container to collect feces as a sample.

2. Description of the Related Art

A container to collect feces as a sample is disclosed, for example, in JP-A-11-64331.

This container includes a suspension storage container storing a suspension and a sample collecting member capable of sealing the suspension storage container. The container is configured to seal the suspension hermetically by inserting the sample collecting member into the suspension storage container to seal the suspension storage container while dispersing feces adhering to the tip end of the sample collecting member in the suspension.

The suspension storage container is a cylindrical container in which one end portion in the longitudinal direction is open so as to be attachable to/detachable from the sample collecting member and the bottom portion is formed by welding a sealing film to the other end portion. During an inspection, the suspension storage container is positioned with the sealing film up, and the suspension is extracted through the nozzle of an inspection system inserted into the suspension storage container by penetrating through the sealing film.

Further, the suspension storage container includes an identification label (attached to the container at the time of manufacturing) laminated on the outer peripheral surface, and according to this label, the name, the sex, and so forth of the subject are specified for the feces collection container. Regarding the lamination of the label, there have been requests for the suspension storage container to secure an area large enough for the subject to write his name and so forth on the label and to make it easier to laminate a label with a bar code issued separately in the hospital or the like on the container besides the identification label. To address these requests, the suspension storage container is formed to have a flat cross-sectional shape.

However, because the suspension storage container of the feces collection container is formed to be flat, in a case where it is transported to the inspection facility or the like, the bottom portion made by welding the sealing film may possibly break when an external force is applied thereon in the minor axis direction. Should it break, the nozzle may not be inserted in a satisfactory manner.

Also, in order to ensure accurate insertion of the nozzle, it is necessary to set the dimension of the flat cross section in the minor axis direction equal to or larger than a specific dimension. However, to form the suspension storage container to be flat to address the requests for the label, the dimension in the major axis direction has to be increased further than in the dimension in the minor axis direction (that is, it has to be set to a dimension larger than the dimension needed to secure the insertion of the nozzle). The sectional area of the container therefore becomes correspondingly larger.

Meanwhile, because the sample collection portion and the nozzle are inserted into the suspension storage container in the axial direction thereof, the suspension has to be present over a sufficiently long region in the axial direction (a certain level has to be ensured as the water level of the suspension). This correspondingly increases a necessary quantity of the filled suspension when the sectional area of the container is increased for the reasons described above, and an extra expense is added to the cost.

The invention was devised in view of the problems discussed above, and therefore has an object to form a suspension storage container in a flat shape for the label to be laminated thereon with ease, and yet to achieve an enhancement of the strength in a direction orthogonal to the major axis direction of the flat cross section and a reduction of a necessary quantity of the suspension.

SUMMARY OF THE INVENTION

In order to solve the problems discussed above, the invention provides a feces collection container including a suspension storage container having an opening at a tip end and capable of storing a suspension inside thereof and a sample collecting member provided with a sample bearing portion at a tip end for a sample made of feces to adhere thereto and attachable to the suspension storage container at the opening at the tip end in a closely-attached state while the sample bearing portion is inserted into the suspension storage container, and configured in such a manner that the sample collecting member is attached to the suspension storage container while the sample bearing portion is dipped in the suspension. The feces collection container is characterized in that: the suspension storage container has a flat portion across a specific region including a tail end; and the flat portion has an outer peripheral wall forming a flat outer peripheral surface and a partition wall extending in a flat cross section of the outer peripheral wall in a direction substantially orthogonal to a major axis direction thereof to partition a chamber inside the outer peripheral wall into plural chambers aligned side by side in the major axis direction, so that the suspension is stored only in part of the plural partitioned chambers, and that a sealing member having an outline almost identical with an outline of the outer peripheral wall is laminated on tail end surfaces of the outer peripheral wall and the partition wall.

According to the invention, because the outer peripheral surface of the outer peripheral wall is formed to be flat, not only is it possible to laminate the label onto the outer peripheral surface with ease, but it is also possible to write in particulars inside the laminated label with ease.

Meanwhile, because the partition wall is formed to extend in the direction substantially orthogonal to the major axis direction to partition the chamber inside the outer peripheral wall into plural chambers aligned side by side in the major axis direction, the strength of the flat portion against an external force in the direction orthogonal to the major axis direction can be enhanced by the presence of the partition wall, which allows the nozzle of the inspection system that penetrates through the sealing member to be accepted in a reliable manner.

Further, in the invention, of the plural chambers partitioned by the partition wall and aligned side by side in the major axis direction, the suspension is stored only in part of the chambers. In other words, because the sectional area of the chamber to store the suspension can be limited to a partial sectional area in the sectional area of the flat portion, in comparison with a case where the suspension is stored in all the chambers inside the flat portion, it is possible to reduce the sectional area of the storage chamber, which can in turn reduce a quantity of the suspension needed to secure a specific water level.

Hence, according to the invention, it is possible to form the suspension storage container in a flat shape for the label to be laminated thereon with ease, and yet to achieve an enhancement of the strength in the direction orthogonal to the major axis direction of the flat cross section and a reduction of a necessary quantity of the suspension.

Also, according to the invention, because the sealing member is laminated to the tail end surfaces of the outer peripheral wall and the partition wall, in comparison with a case where the sealing member is laminated to the tail end surface of the outer peripheral wall alone, the lamination area for the sealing member can be increased, which can in turn enhance the lamination strength of the sealing member.

The major axis direction referred to herein means a direction in which the diameter (side) having the longest dimension in the flat section of the flat portion extends, and the specific region means a region onto which at least the label can be laminated.

BRIEF DESCRIPTION OF THE DRAWINGS

FIG. 4 is a side view of the sample collecting member when feces are attached thereto.

FIGS. 5A, 5B, and 5C are sectional front views of the suspension storage container and the sample collecting member when they are attached to each other, respectively showing a state of the both components before threaded engagement, a state of the both components in the middle of threaded engagement, and a state of the both components when the threaded engagement is completed.

DETAILED DESCRIPTION OF THE PREFERRED EMBODIMENTS

Hereinafter, preferred embodiments of the invention will be described with reference to the drawings.

Figure 1A:
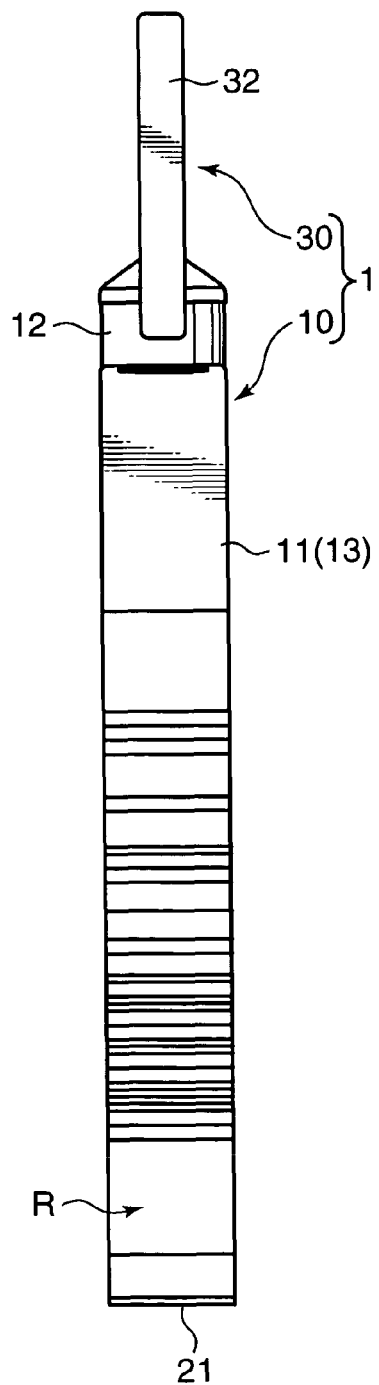
FIG. 1A is a side view and FIG. 1B is a front view of a feces collection container according to one embodiment of the invention.
Figure 1B:
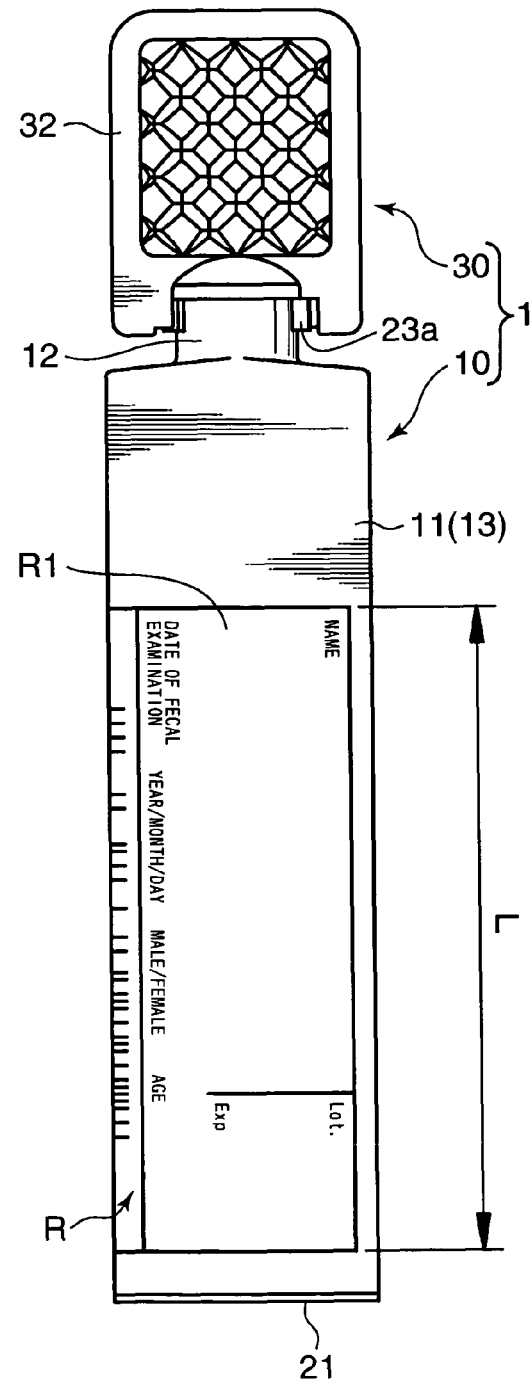
Figure 2A:
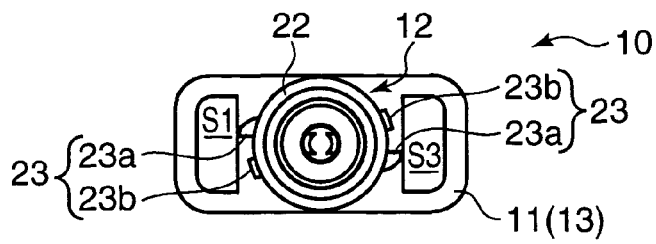
FIG. 2A is a plan view.
Figure 2B:
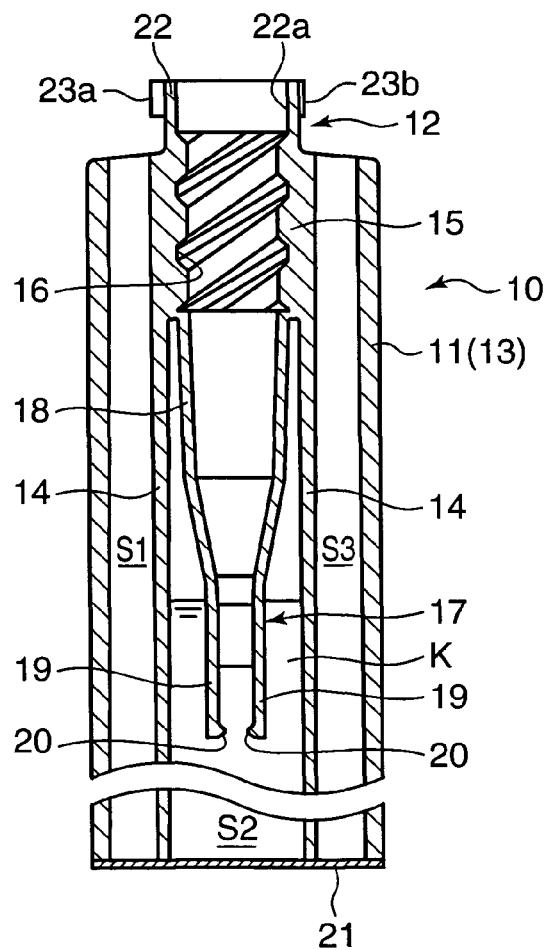
FIG. 2B is a sectional front view.
Figure 2D:
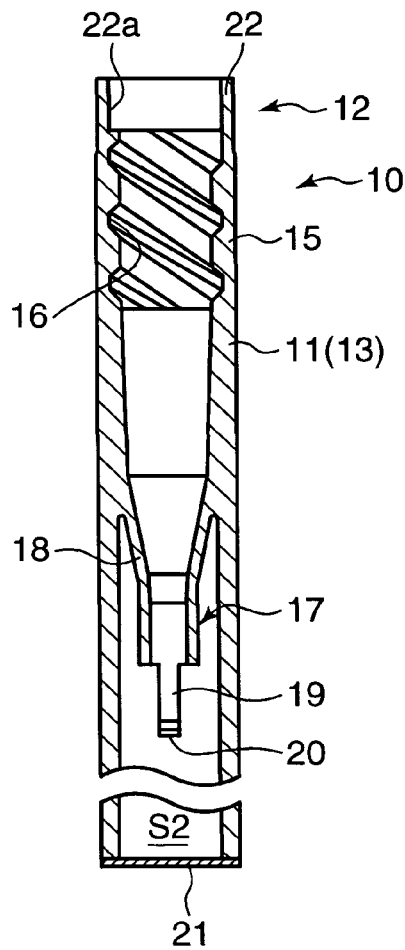
FIG. 2D is a sectional side view of a suspension storage container of FIG. 1.
Figure 2C:
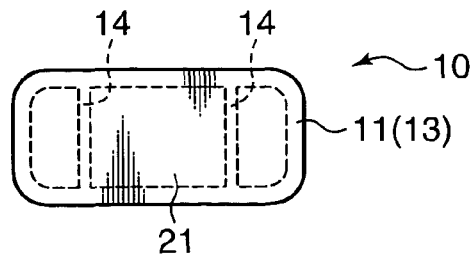
FIG. 2C is a bottom view.
Figure 3A:
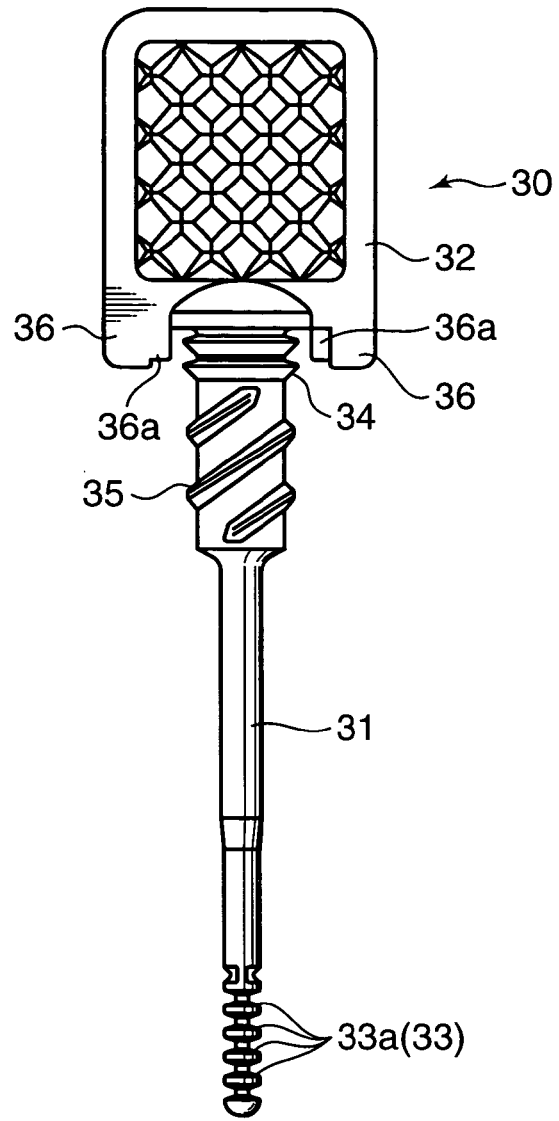
FIG. 3A is a front view and FIG. 3B is a bottom view of a sample collecting member of FIG. 1.
Figure 3B:
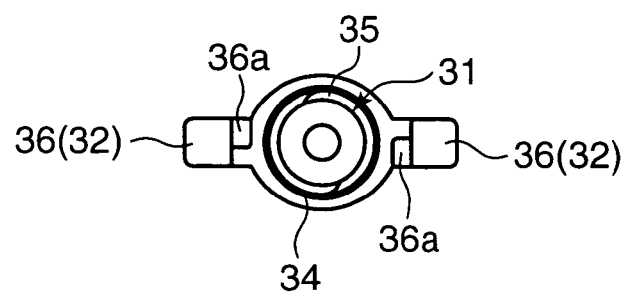

FIG. 1A is a side view and FIG. 1B is a front view of a feces collection container 1 according to one embodiment of the invention. FIG. 2A is a plan view, FIG. 2B is a sectional front view, FIG. 2C is a bottom view, and FIG. 2D is a sectional side view of a suspension storage container 10 of FIG. 1. FIG. 3A is a front view and FIG. 3B is a bottom view of a sample collecting member 30 of FIG. 1.

With reference to the respective drawings, the feces collection container 1 is formed by combining the suspension storage container 10 and the sample collecting member 30.

The suspension storage container 10 includes a container main body 11 storing a suspension K and a connection port (opening at the tip end) 12 protruding toward the tip end (the upper side in FIG. 2) of the container main body 11 as shown in FIG. 2B, and these container main body 11 and connection port 12 are molded in one piece from light-transmitting synthetic resin.

In the container main body 11 of this embodiment, a chamber formed in a flat shape inside an outer peripheral wall 13 is partitioned by a pair of partition walls 14 extending in a direction substantially orthogonal to the major axis direction of the flat cross section of the outer peripheral wall 13, and it is configured in such manner so as to store the suspension K only in a chamber S2 defined between these partition walls 14, which is a chamber whose both ends are clogged with a top board 15 and a sealing film 21 while the sample collecting member 30 is inserted into a female screw portion 16. Hereinafter, the concrete configuration will be described.

The main body portion 11 is of a flat shape across the entire area from the bottom portion side (tail end side) to the tip end side. To be more concrete, the container main body 11 has the outer peripheral wall 13 that forms a flat outer peripheral surface having a substantially rectangular cross section, and a pair of partition walls 14 extending in a direction substantially orthogonal to the major axis direction of the flat cross section of the outer peripheral wall 13. These partition walls 14 partition the chamber inside the outer peripheral wall 13 into three chambers S1 through S3 aligned side by side in the major axis direction. As has been described, because the respective partition walls 14 are provided on the inner side of the outer peripheral wall 13, even when an external force is conferred to the outer peripheral wall 13 in the direction orthogonal to the major axis direction of the flat cross section, the container main body 11 is able to withstand the external force by means of the both partition walls 14.

A subject identification label R is laminated on the outer peripheral surface 13 from the front surface to the side surface, and a subject's entry space R1 of the label R is positioned on the broad surface of the outer peripheral wall 13 (the surface along the major axis direction of the outer peripheral wall 13). As has been described, because the label R is laminated on the flat outer peripheral surface of the outer peripheral wall 13, the lamination work can be performed with relative ease. Meanwhile, because the subject's entry space R1 of the label R is positioned on the broad surface, the subject is able to write in particulars inside the entry space R1 with ease.

Further, the container main body 11 includes the top board 15 provided on the tip end side of the chamber S2 and penetrating toward the tip end, the female screw portion 16 formed on the inner surface of a through-hole in the top board 15, and a leveling portion 17 extending from the top board 15 toward the bottom portion (the lower side in FIG. 2). The female screw portion 16 and the leveling portion 17 are positioned almost concentrically.

The leveling portion 17 includes a cylinder portion 18 extending from the top board 15 toward the bottom portion and tapered on the tip end side, a pair of leg portions 19 extending from the tip end portion of the cylinder portion 18 toward the bottom portion, and scraping claws 20 protruding inward at the tip end portions of the leg portions 19.

The chambers S1 through S3 are open toward the bottom portions, and a sealing film (sealing member) 21 is laminated to the bottom surface of the container main body 11 to clog these openings. In this embodiment, the chambers S1 and S3 are formed to be open straight also on the tip end side.

The sealing film 21 has an outline almost identical with the outline of the flat cross section of the outer peripheral wall 13 (that is, a rectangular outline), and forms the bottom portion of the container main body 11 for the suspension K to be stored within the chamber S2 by being laminated onto the bottom surfaces (tail end surfaces) of the outer peripheral wall 13 and the respective partition walls 14 by means of thermal welding or the like.

In this embodiment, of the chambers S1 through S3 partitioned by the both partition walls 14, the suspension K is stored only in the chamber S2 using the sealing film 21 as the bottom portion. Hence, in comparison with a case where the suspension K is stored in all the chambers (S1+S2+S3) inside the outer peripheral wall 13, the sectional area of a storing portion of the suspension K can be reduced. It is thus possible to set a quantity of the suspension K needed to secure a specific water level to a relatively small quantity.

Further, regarding the welding of the sealing film 21, because the partition walls 14 are provided to the outer peripheral wall 13, the welding area of the sealing film 21 can be increased in comparison with a case where the sealing film 21 is welded to the bottom surface of the outer peripheral wall 13 alone. It is thus possible to enhance the welding strength of the sealing film 21.

Meanwhile, the connection port 12 is provided to stand on the top board 15, and includes a cylinder portion 22 linked to the female screw portion 16 almost concentrically and a pair of locking portions 23 formed on the outer peripheral surface at the tip end of the cylinder portion 22.

The respective locking portions 23 are positioned oppositely in the major axis direction of the flat cross section of the outer peripheral wall 13, and each includes a locking claw 23a and a snapping protrusion 23b. The locking claws 23a as well as the snapping protrusions 23b are provided at positions to be point symmetry by 180° about the axis line of the cylinder portion 22. For each locking portion 23, the dimension of a space between the locking claw 23a and the snapping protrusion 23b is set to a dimension sufficient to accommodate a handle portion 32 described below in the thickness direction. Further, each locking portion 23 is configured to engage with a protrusion 36a described below so as to lock the suspension storage container 10 and the sample collecting member 30 at a specific rotational position (thread engagement operation completing point).

The sample collecting member 30 is a synthetic resin molding including a collecting rod 31 and the handle portion 32 formed at one end portion (the top end portion in FIG. 3) of the collecting rod 31 as a single piece.

A sample bearing portion 33 is formed at the tip end (the lower side in FIG. 3) of the collecting rod 31, and a pair of sealing flanges 34 is formed at the end portion on the opposite side (the upper side in FIG. 3). In addition, a male screw portion 35 is formed somewhere between the sample bearing portion 33 and the sealing flanges 34.

The sample bearing portion 33 is formed on the outer peripheral surface of the collecting rod 31 around the axis line thereof, and comprises plural concave grooves 33a aligned side by side in the axis line direction. Each of these concave grooves 33a is set to have a groove width dimension sufficient to accommodate the scraping claws 20.

Each sealing flange 34 is formed to swell outward from the outer peripheral surface of the colleting rod 31, and the dimension thereof is set so as to achieve a liquid-tight state in a space between the collecting rod 31 and a bore portion 22a of the cylinder portion 22 when inserted into the bore portion 22a along the axis line.

Meanwhile, the handle portion 32 is an almost rectangular plate-shaped member, and a net-like pattern is embossed by forming plural digging portions in the frontal stem portion. This pattern functions as a slip stopper when the user pinches the handle portion 32.

In addition, the handle portion 32 is provided with a pair of leg portions 36 protruding from the both side portions of the collecting rod 31 toward the tip ends (toward the lower side in FIG. 3), and each of the leg portions 36 is provided with the locking protrusion 36a that faces inward.

A fecal inspection method using the feces collection container 1 described above will now be described.

Initially, as is shown in FIG. 4, the user pinches the handle portion 32 of the sample collecting member 30 and pushes and rubs the tip end of the collecting rod 31 against the feces as the sample for the sample to come into the respective concave grooves 33a formed in the tip end. It should be noted that because the handle portion 32 is formed to be flat, the user is able to pinch the handle portion 32 with ease using the first and second fingers.

Subsequently, as shown in FIG. 5A, the user turns up the connection port 12 and inserts the sample collecting member 30 into the suspension storage container 10 storing the suspension K only in the chamber S2 between the both partition walls 14 through the connection port 12 from the sample bearing portion 33 side. It should be noted that because it is configured to store the suspension K only in the chamber S2 among the respective chambers S1 through S3 partitioned by the both partition walls 14, the sectional area of the storing portion can be set to be relatively small, which ensures a high water level even when a quantity of the used suspension K is relatively small. It is thus possible to dip the sample bearing portion 33 in the suspension K as soon as it is inserted.

When the sample collecting member 30 is inserted, as the sample bearing portion 33 passes through the tapered portion of the cylinder portion 18, extra feces adhering onto the surface of the collecting rod 31 are leveled off by the tapered inner surface of the cylinder portion 18 and removed inside the cylinder portion 18.

Subsequently, as is shown in FIG. 5B, the user rotates the handle portion 32 (sample collecting member 30) with respect to the suspension storage container 10 while he keeps pinching the handle portion 32 for the screw portions 16 and 35 to be threadably engaged with each other. This allows the sample collecting member 30 to be inserted into a deeper portion of the suspension storage container 10 as it rotates with respect to the suspension storage container 10.

In the process of the threaded engagement, each scraping claw 20 surmounts the convex portion between the respective concave groove 33a and goes into the following concave groove 33a as the sample collecting member 30 travels straight by a distance comparable to the pitch of each concave groove 33a. Meanwhile, the scraping claw 20 coming into the concave groove 33a in this manner undergoes relative displacement therein in the circumferential direction in response to a rotational operation performed while the sample collecting member 30 travels straight by the pitch. Accordingly, the feces inside the respective concave grooves 33a are successively scraped off inside the chamber S2 in a reliable manner to be dispersed in the suspension K.

By further tightening both the screw portions 16 and 35, as is shown in FIG. 5C, the feces scraping operation is completed for all the concave grooves 33a, and a liquid-tight state is established in a space between the collecting rod 31 and the connection port 12 by the sealing flanges 34 while the rotational position of the sample collecting member 30 with respect to the suspension storage container 10 is locked.

Figure 6A:
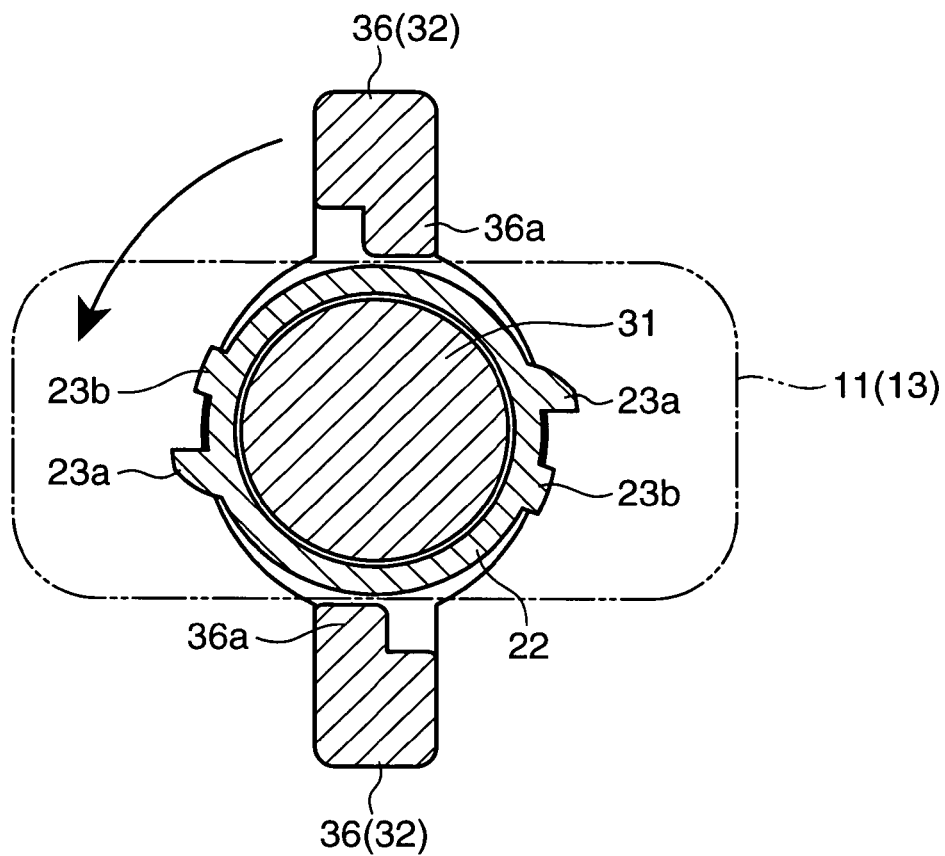
FIG. 6A is a cross section taken along the line VI(A)-VI(A) of FIG. 5
Figure 6B:
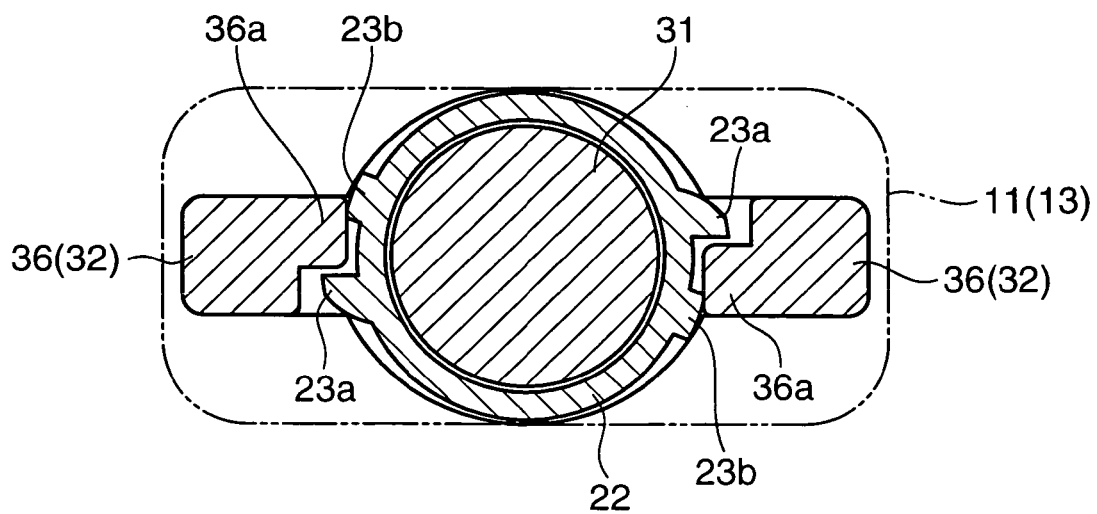
FIG. 6B is a cross section taken along the line VI(B)-VI(B) of FIG. 5, showing the rotational position of the suspension storage container and the sample collecting member.

FIG. 6 is a view showing the rotational position of the suspension storage container 10 and the sample collecting member 30. FIG. 6A is a cross section taken along the line VI(A)-VI(A) of FIG. 5 and FIG. 6B is a cross section taken along the line VI(B)-VI(B) of FIG. 5.

More specifically, by further tightening the sample collecting member 30 from the rotational position shown in FIG. 6A, as is shown in FIG. 6B, each protrusion 36a provided to the handle portion 32 surmounts the snapping protrusion 23b of the connection port 12 and is brought into a state where it is pressed against the side surface of the locking claw 23a (the rotational position of the sample collecting member 30 at this point in time is the threaded engagement operation completing position).

At the threaded engagement operation completing position, the handle portion 32 (each protrusion 36a) is positioned in a space between the snap protrusion 23b and the locking claw 23a. Hence, not only it is possible to limit further rotations in the tightening direction by the locking claws 23a, but it is also possible to make rotations in the loosening direction of both the screw portions 16 and 35 almost infeasible by the snapping protrusions 23b.

The user then detects that the sample collecting member 30 reaches the desired threaded engagement operation completing position by the feel of the protrusions 36a surmounting the snapping protrusion 23b (the feel of clicking), and becomes aware that the sample collecting member 30 can no longer be rotated as the protrusions 36a are now being pressed against the locking claws 23a.

Further, in this state, because the handle portion 32 (each protrusion 36a) is positioned in a space between the snap protrusion 23b and the locking claw 23a, it is present at the position at which the width direction thereof (the long side direction of the flat cross section) is brought almost into agreement with the long side direction of the flat cross section of the outer peripheral wall 13 (a position at which it fits inside the contour of the outer peripheral wall 13 when viewed in a plane).

The feces collection container 1 brought into the state of FIG. 5C is then transported to an appropriate inspection facility. Regarding the transportation, the user writes in particulars, such as the name, the sex, and so forth inside the subject's entry space R1 of the label R laminated onto the container main body 11 (see FIG. 1). Herein, because the entry space R1 is laminated on the flat surface parallel to the major axis direction of the flat cross section of the outer peripheral wall 13, the user is able to write in particulars with ease.

In the transportation process of the feces collection container 1, because each partition wall 14 is formed to extend in the direction substantially orthogonal to the major axis direction of the flat cross section of the outer peripheral wall 13, even when an external force in the direction orthogonal to the major axis direction is conferred to the container main body 11, the container main body 11 is able to withstand the external force by means of the both partition walls 14. It is thus possible to prevent the outer peripheral wall 13, in particular, the bottom portion thereof to which the sealing film 21 is welded, from breaking in the direction orthogonal to the major axis direction as much as possible, which in turn allows the nozzle N of the inspection system that is inserted therein later to be accepted in a reliable manner.

When the feces collection container 1 is transported to the inspection facility, the sample is inspected by the inspection system installed therein.

Figure 7:
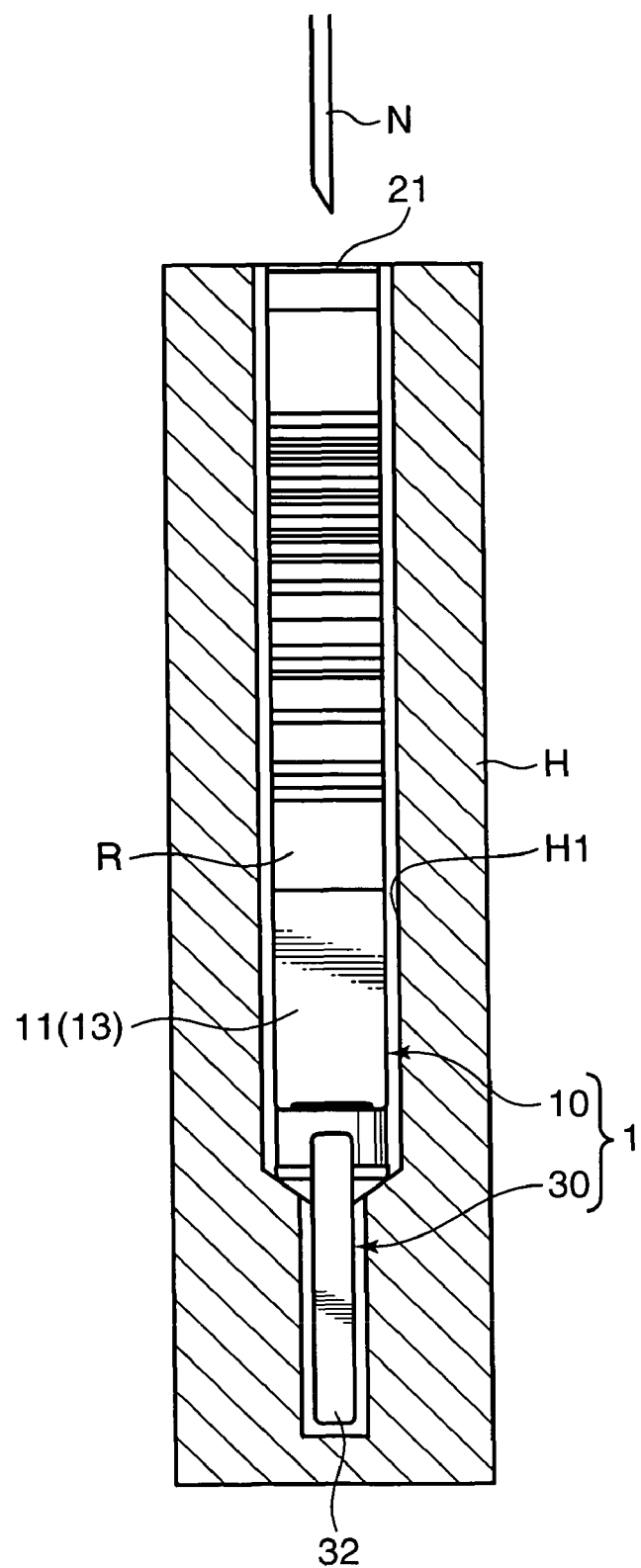
FIG. 7 is a sectional side view showing a work to extract the suspension inside the feces collection container through the nozzle of an inspection system.

To be more concrete, in the inspection facility, as is shown in FIG. 7, the feces collection container 1 is attached to a holder H in the shape of a container having a holding hole H1 formed along the outline of the feces collection container 1 to be open upward with the sealing film 21 up, and the holder H is set in the inspection system. It should be noted that because the suspension storage container 10 and the handle portion 32 are locked at the thread engagement operation completing position by the respective locking portions 23 and the protrusion 36a, there is no need for a work to separately check the positioning of the handle portion 32 and the suspension storage container 10 while the feces collection container 1 is being inserted into the holder H. It is therefore possible to reduce the labor involved in the inspection work.

Subsequently, the inspection system lowers the nozzle N to be inserted into a space between the both partition walls 14 of the container main body 11 (that is, the chamber S2) by breaking through the sealing film 21. It should be noted that the suspension K is stored only in the chamber S2 defined by the both partition walls 14, that is, it is stored only in a part of chambers inside the outer peripheral wall 13. Hence, in comparison with a case where the suspension K is stored in all the chambers (S1+S2+S3) of the outer peripheral wall 13, it is possible to limit the sectional area of a portion to store the suspension K. It is thus possible to ensure a water level corresponding to the descended position of the nozzle N (a water level at which the tip end portion of the nozzle N can be dipped in the suspension K) even when a quantity of the used suspension K is relatively small (2 ml in this embodiment).

The inspection system then sucks in the suspension K through the nozzle N inserted into the suspension K inside the chamber S2 for extraction, and performs a specific inspection on the suspension K.

As has been described, according to the feces collection container 1, because the outer peripheral surface of the outer peripheral wall 13 is formed to be flat, not only is it possible to laminate the label R on this outer peripheral surface with ease, but it is also possible to enable the subject to write in particulars inside the entry space R1 of the laminated label R with ease.

Meanwhile, the partition walls 14 are formed to extend in the direction substantially orthogonal to the major axis direction to partition the chamber inside the outer peripheral wall 13 into three chambers S1 through S3 aligned side by side in the major axis direction. The strength of the flat portion (the container main body 11 in this embodiment) against an external force in the direction orthogonal to the major axis direction can be therefore enhanced by the presence of the partition walls 14, which allows the nozzle N of the inspection system that penetrates through the sealing film 21 to be accepted in a reliable manner.

Further, the feces collection container 1 is configured to store the suspension K only in the chamber S2 defined by the partition walls 14. In other words, the sectional area of the chamber to store the suspension K can be limited to a partial sectional area in the sectional area of the container main body 11. Hence, in comparison with a case where the suspension K is stored in all the chambers of the container main body 11, it is possible to reduce the sectional area of the storage chamber, which can in turn reduce a quantity of the suspension K needed to secure a specific water level.

Hence, according to the feces collection container 1, it is possible to make the suspension storage container 10 in a flat shape for the label to be laminated thereon with ease, and yet to achieve an enhancement of the strength in the direction orthogonal to the major axis direction of the flat cross section and a reduction of a necessary quantity of the suspension K.

Also, in the feces collection container 1, the sealing film 21 is welded to the bottom surfaces (tail end surfaces) of the outer peripheral wall 13 and the partition walls 14. In comparison with a case where the sealing film 21 is welded to the tail end surface of the outer peripheral wall 13 alone, it is possible to increase the welding area for the sealing film 21, which can in turn enhance the welding strength of the sealing film 21.

For example, in order to secure the welding strength between the sealing film 21 and the suspension storage container 10, the related art adopts a scheme by which the suspension storage container 10 is provided with a flange portion that is formed to swell outward in a region including the tail end surface, and the sealing film 21 is welded to this flange portion. On the contrary, according to the feces collection container 1, the welding area for the sealing film 21 can be increased not only by providing the flange portion as described above, but also by increasing the thickness of the partition walls 14.

In a case where the flange portion is formed as described above, there are problems, for example, when the feces collection container 1 is inserted into a bag used for transportation to the inspection facility or the like, the feces collection container 1 cannot be handled easily because the flange portion hooks into the bag or when a large number of feces collection containers 1 each placed into the bag are transported, they become bulky and will not fit easily. In view of the foregoing, it is more preferable to increase the welding area for the sealing film 21 by adjusting the thickness of the partition walls 14 rather than by providing the flange portion.

Also, because the feces collection container 1 stores the suspension K in a space between a pair of the partition walls 14, the both sides of the portion (chamber S2) storing the suspension K can be supported by the respective partition walls 14. It is thus possible to prevent the breaking of the chamber S2 at the flat portion, in particular, the bottom portion to which the sealing film 21 is welded, in a more reliable manner.

Further, by storing the suspension K in a space between the respective partition walls 14, it is possible to place (store) the suspension K on the center side of the suspension storage container 10 in the long side direction, which can bring the feces collection container 1 into good balance.

According to the configuration in which the short sides of the outer peripheral wall 13 and the partition walls 14 are made almost parallel to each other, the flat portion is able to withstand an external force in the short side direction by means of both the short sides and the partition walls 14. It is thus possible to further enhance the strength of the flat portion against an external force in the short side direction.

According to the configuration in which the outer peripheral wall 13 and the partition walls 14 are formed almost across the entire area of the suspension storage container 10 as with the feces collection container 1, because the outer peripheral surface of the suspension storage container 10 is formed to be flat almost across the entire area, it is possible to set a broader lamination range for the label R. At the same time, because the partition walls 14 are provided almost across the entire area of the suspension storage container 10, it is possible to enhance the strength against an external force in the direction orthogonal to the major axis direction of the flat cross section of the flat portion almost across the entire area of the suspension storage container 10.

Further, according to the feces collection container 1, because the chamber inside the suspension storage container 10 is partitioned across the entire area by the partition walls 14, it is possible to reduce the sectional area of the chamber to store the suspension K almost across the entire area of the suspension storage container 10. A necessary quantity of the suspension K can be therefore reduced as much as possible.

According to the configuration in which the sample collecting member 30 and the suspension storage container 10 are threadably engaged with each other by means of the screw portions 16 and 35, it is possible to prevent an unexpected separation of the suspension storage container 10 and the sample collecting member 30 that are attached to each other in a closely-attached state after the sample is collected as much as possible. In particular, in a case where the feces collection container 1 is transported to the inspection facility or the like by mail or any other similar means, by adopting this configuration, it is possible to prevent a trouble, such as leakage of the suspension K during transportation, in a reliable manner.

According to the configuration in which the flat handle portion 32 and the respective locking portions 23 and protrusions 36a (locking mechanism) that allow the suspension storage container 10 and the sample collecting member 30 to engage with each other at a specific rotational position are provided, when the sample is collected, the user is able to pinch the flat handle portion 32 between, for example, the first and second fingers. The portability of the sample collecting member 30 can be therefore enhanced. Meanwhile, in a case where the handle portion 32 and the suspension storage container 10 are attached to each other through threaded engagement, they are locked at the position (threaded engagement operation completing position) at which their respective major axis directions are brought into agreement with each other by the locking mechanism. It is thus possible to make the feces collection container 1 compact after the sample is collected.

Meanwhile, according to the configuration in which the scraping claws 20 and the concave grooves 33a undergo relative displacement in response to a tightening operation of both the screw portions 16 and 35, the feces collected in the respective concave grooves 33a can be scraped off in a reliable manner inside the sample storage container 10 in association with the threaded engagement of both the screw portions 16 and 35. It is thus possible to disperse the feces in the suspension K in a reliable manner after the sample collecting member 30 and the suspension storage container 10 are attached to each other.

Incidentally, of the chambers S1 through S3 of the feces collection container 1, it is possible to fill the chambers S1 and S3 storing no suspension K with a cooling agent, such as a gel of water-absorbing polymer. According to this configuration, even in a case where the feces collection container 1 is transported over a long period, the suspension K can be maintained at a low temperature over a long period by means of the cooling agent. It is thus possible to prevent a change with time, such as a reduction in quantity of the component to be inspected (for example, hemoglobin) dispersed in the suspension K, as much as possible while utilizing the chamber S1 or S3 effectively.

In the embodiment described above, the chamber inside the outer peripheral wall 13 is partitioned into three chambers S1 through S3 by means of a pair of the partition walls 14, and the suspension K is stored in one of the chambers S1 through S3, that is, the chamber S2. The invention, however, is not limited to this configuration, and for example, a through-hole may be provided in one of the partition walls 14 to bring the chambers S1 and S2 into communication with each other while the openings at the tip end side of both the chambers S1 and S2 are clogged with the top board 15, so that the suspension K is stored in both the chambers S1 and S2. To bring both the chambers S1 and S2 in communication with each other, one of the partition walls 14 may be formed shorter so as to end just before the top board 15.

According to the configuration in which the suspension K is stored in plural continuous chambers S1 and S2 as has been described, in comparison with a case where the suspension K is stored throughout the suspension storage container 10, it is also possible to reduce the sectional area of the portion to store the suspension K. Hence, as with the embodiment described above, a necessary quantity of the suspension K can be reduced.

Also, the embodiment above has described the configuration in which the outer peripheral wall 13 and the partition walls 14 are provided across the entire area of the suspension storage container 10 (that is, the configuration in which the container main body 11 is equivalent to the flat portion). The invention, however, is not limited to this configuration, and for example, the configuration of FIG. 8 is also applicable.

Figure 8:
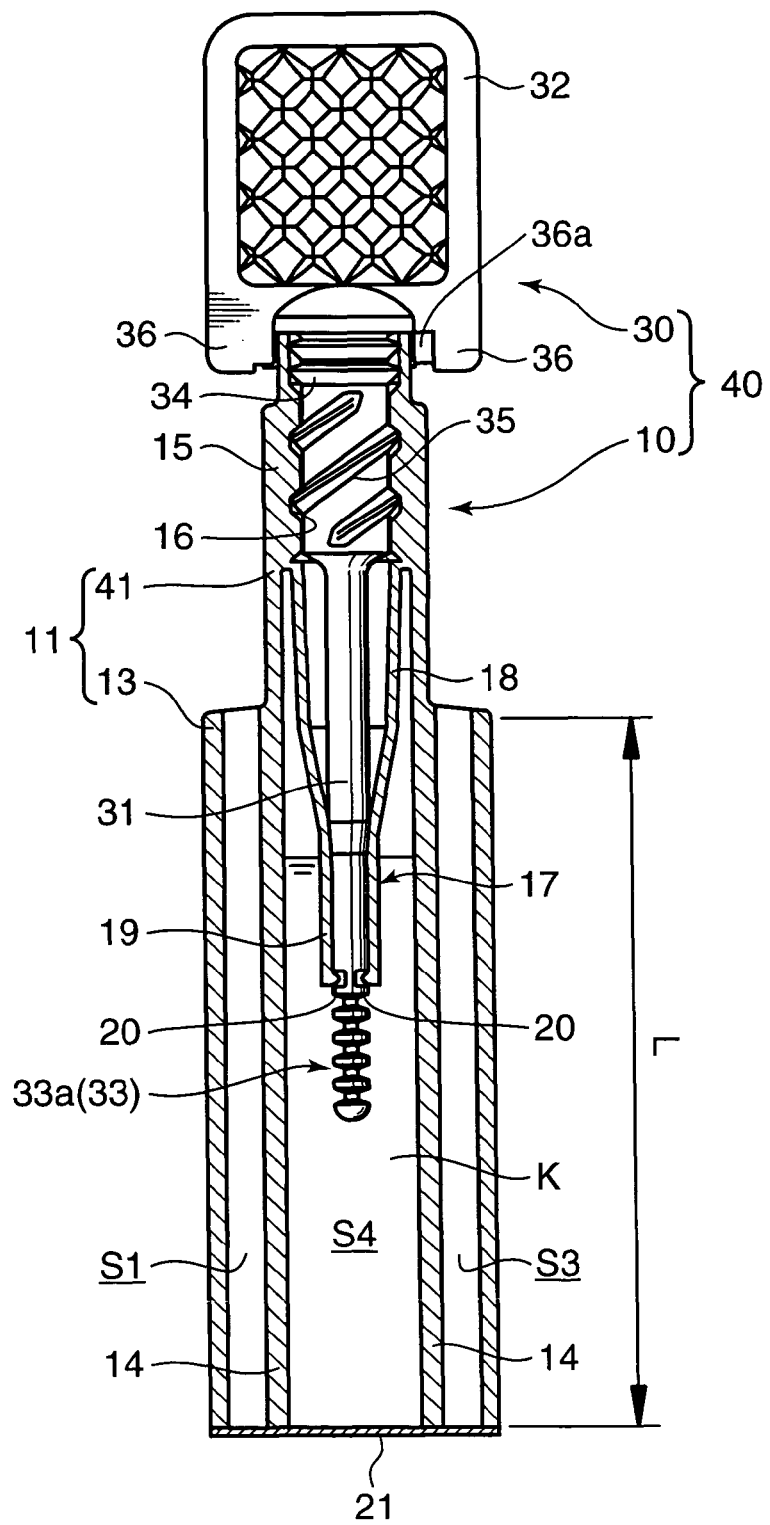
FIG. 8 is a sectional front view of a feces collection container according to another embodiment.

A feces collection container 40 of FIG. 8 is different from the embodiment above, and configured in such a manner that the outer peripheral wall 13 is made shorter on the bottom surface side.

To be more concrete, the container main body 11 of the feces collection container 40 includes the outer peripheral wall 13 made shorter than the counterpart in the embodiment above, and a cylindrical storing portion 41 formed in a space between the outer peripheral wall 13 and the connection port 12. It is therefore configured to store the suspension K in a chamber S4 defined by the cylindrical storing portion 41 and the both partition walls 14.

When the outer peripheral wall 13 is made shorter, the longitudinal dimension thereof has to be at least equal to or larger than the width dimension L (see FIG. 1) of the label R.

The feces collection container 40 is also configured to store the suspension K in the portion defined by the both partition walls 14 inside the outer peripheral wall 13. Hence, in comparison with a case where the suspension K is stored throughout the interior of the outer peripheral wall 13, it is possible to reduce the sectional area of the portion to store the suspension K. A necessary quantity of the suspension K can be therefore reduced.

Further, because the longitudinal dimension of the outer peripheral wall 13 can be as short as the width dimension L of the label R in the feces collection container 40, a synthetic resin material or the like needed to mold the container main body 11 can be reduced, which can in turn save the cost of the feces collection container 40.

In addition, each embodiment above has the configuration that a pair of the partition walls 14 is provided. The invention, however, is not limited to this configuration, and for example, the configuration shown in FIG. 9 is also applicable.

Figure 9A:
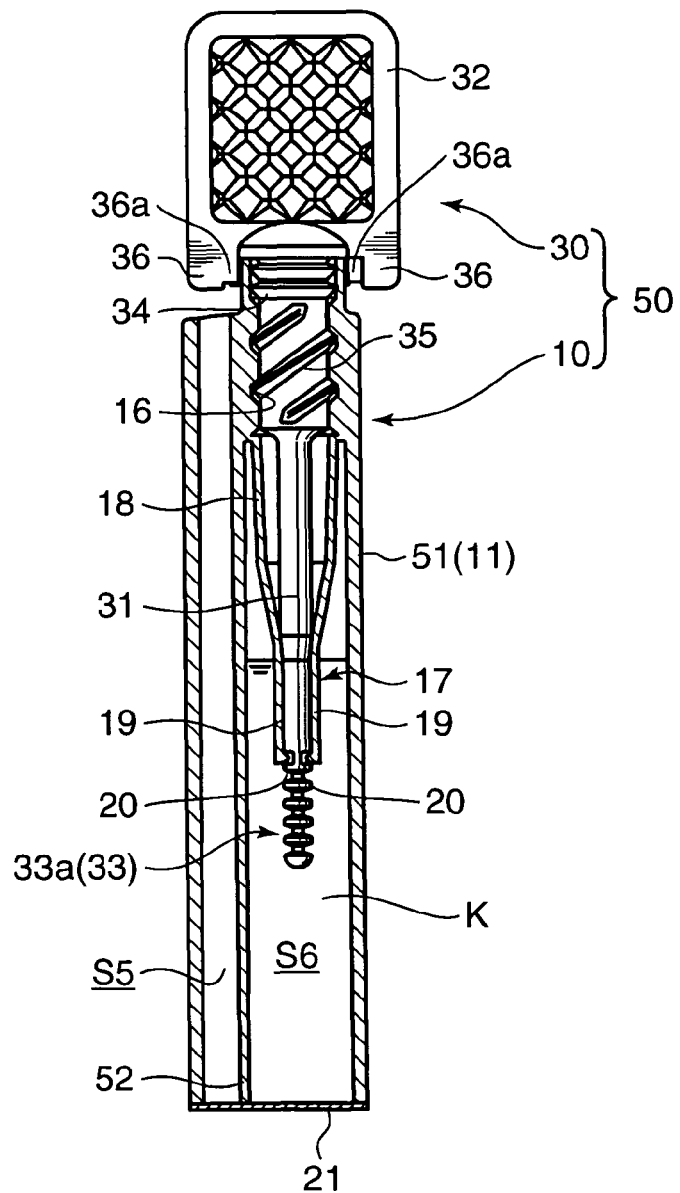
FIG. 9 is a sectional front view of a feces collection container according to still another embodiment.
Figure 9B:
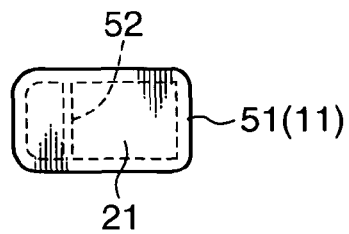

A feces collection container 50 of FIG. 9 is different from the respective embodiments described above. It includes an outer peripheral wall 51 forming a flat outer peripheral surface having an almost rectangular cross section, and a partition wall 52 extending in a direction substantially orthogonal to the major axis direction of the flat cross section of the outer peripheral wall 51 to partition the chamber inside the outer peripheral wall 51 into two chambers S5 and S6 aligned side by side in the major axis direction. It is therefore configured to store the suspension K in the chamber S6.

With this feces collection container 50, too, because the outer peripheral wall 51 forms the flat outer peripheral surface of an almost rectangular shape, the readiness to laminate the label R and the readiness to write in particulars inside the entry space R1 (see FIG. 1) can be ensured. Further, because the partition wall 52 is formed to extend in the short side direction of the outer peripheral wall 51, it is possible to enhance the strength of the outer peripheral wall 51 against an external force in the short side direction.

In the respective embodiments described above, the outer peripheral walls 13 and 51 form the outer peripheral surfaces each having an almost rectangular cross section. It is, however, sufficient that the outer peripheral wall forms at least the flat outer peripheral surface to make it easy to laminate the label R or to make it easy to write in particulars inside the entry space R1, and for example, the outer peripheral wall may form an outer peripheral surface having an elliptical cross section.

More specifically, the invention of the embodiments described above is a feces collection container including a suspension storage container having an opening at a tip end and capable of storing a suspension inside thereof and a sample collecting member provided with a sample bearing portion at a tip end for a sample made of feces to adhere thereto and attachable to the suspension storage container at the opening at the tip end in a closely-attached state while the sample bearing portion is inserted into the suspension storage container, and configured in such a manner that the sample collecting member is attached to the suspension storage container while the sample bearing portion is dipped in the suspension. The feces collection container is characterized in that: the suspension storage container has a flat portion across a specific region including a tail end; and the flat portion has an outer peripheral wall forming a flat outer peripheral surface and a partition wall extending in a flat cross section of the outer peripheral wall in a direction substantially orthogonal to a major axis direction thereof to partition a chamber inside the outer peripheral wall into plural chambers aligned side by side in the major axis direction, so that the suspension is stored only in part of the plural partitioned chambers, and that a sealing member having an outline almost identical with an outline of the outer peripheral wall is laminated on tail end surfaces of the outer peripheral wall and the partition wall.

According to the invention, because the outer peripheral surface of the outer peripheral wall is formed to be flat, not only is it possible to laminate the label onto the outer peripheral surface with ease, but it is also possible to write in particulars inside the laminated label with ease.

Meanwhile, because the partition wall is formed to extend in the direction substantially orthogonal to the major axis direction to partition the chamber inside the outer peripheral wall into plural chambers aligned side by side in the major axis direction, the strength of the flat portion against an external force in the direction orthogonal to the major axis direction can be enhanced by the presence of the partition wall, which allows the nozzle of the inspection system that penetrates through the sealing member to be accepted in a reliable manner.

Further, in the invention, of the plural chambers partitioned by the partition wall and aligned side by side in the major axis direction, the suspension is stored only in part of the chambers. In other words, because the sectional area of the chamber to store the suspension can be limited to a partial sectional area in the sectional area of the flat portion, in comparison with a case where the suspension is stored in all the chambers inside the flat portion, it is possible to reduce the sectional area of the storage chamber, which can in turn reduce a quantity of the suspension needed to secure a specific water level.

Hence, according to the invention, it is possible to form the suspension storage container in a flat shape for the label to be laminated thereon with ease, and yet to achieve an enhancement of the strength in the direction orthogonal to the major axis direction of the flat cross section and a reduction of a necessary quantity of the suspension.

Also, according to the invention, because the sealing member is laminated to the tail end surfaces of the outer peripheral wall and the partition wall, in comparison with a case where the sealing member is laminated to the tail end surface of the outer peripheral wall alone, the lamination area for the sealing member can be increased, which can in turn enhance the lamination strength of the sealing member.

The major axis direction referred to herein means a direction in which the diameter (side) having the longest dimension in the flat section of the flat portion extends, and the specific region means a region onto which at least the label can be laminated.

In the feces collection container described above, it is preferable that the flat portion has a pair of partition walls aligned side by side inside the outer peripheral wall in the major axis direction thereof, and the suspension is stored in a space between the partition walls.

According to the configuration in which the suspension is stored in a space between a pair of partition walls aligned side by side in the major axis direction, the both sides of a portion storing the suspension can be supported by the respective partition walls. It is thus possible to prevent breaking of the flat portion in the portion storing the suspension, in particular, the bottom portion to which the sealing film is laminated.

Also, according to the configuration described above, because the suspension is stored in a space between a pair of partition walls, it is possible to place (store) the suspension on the center side of the suspension storage container in the major axis direction, which can bring the feces collection container into good balance.

In the feces collection container described above, it is preferable that the outer peripheral wall has a cross section almost in a shape of a rectangle, and the partition wall extends in a direction almost parallel to short sides of the rectangle.

According to the configuration in which the short sides of the outer peripheral wall having an almost rectangular cross section and the partition wall(s) are made parallel to each other, the flat portion is able to withstand an external force in the short side direction by means of both the short sides and the partition wall(s). It is thus possible to further enhance the strength of the flat portion against an external force in the short side direction.

In the feces collection container described above, it is preferable that the flat portion is formed almost across an entire area of the suspension storage container.

According to the configuration in which the flat portion is formed almost across the entire area of the suspension storage container, because the outer peripheral surface of the suspension storage container is formed to be flat almost across the entire area, it is possible to set a broader lamination range for the label. At the same time, because the partition wall/partition walls is/are provided almost across the entire area of the suspension storage container, it is possible to enhance the strength against an external force in the direction orthogonal to the major axis direction of the flat cross section of the flat portion almost across the entire area of the suspension storage container.

Further, according to the configuration described above, because the chamber inside the suspension storage container is partitioned across the entire area by the partition wall(s), it is possible to reduce the sectional area of the chamber to store the suspension across the entire area of the suspension storage container. A necessary quantity of the suspension can be therefore reduced further.

In the feces collection container described above, it is preferable that: the suspension storage container includes a screw portion formed at the opening at the tip end and the sample collecting member includes a flat handle portion formed at an end portion on an opposite side to the sample bearing portion and a screw portion formed somewhere between the handle portion and the sample bearing portion, and the feces collection container is configured in such a manner that the suspension storage container and the sample collecting member are attachable to each other through threaded engagement of the both screw portions; the feces collection container includes a locking mechanism that allows the suspension storage container and the sample collecting member to engage with each other at a specific rotational position; and the locking mechanism defines a threaded engagement operation completing position at which a major axis direction of the handle portion and a major axis direction of the flat portion of the suspension storage container are brought almost into agreement with each other.

According to the configuration in which the sample collecting member and the suspension storage container are threadably engaged with each other by means of the screw portions, it is possible to prevent an unexpected separation of the suspension storage container and the sample collecting member that are attached to each other in a closely-attached state after the sample is collected as much as possible. In particular, in a case where the feces collection container is transported to the inspection facility or the like by mail or any other similar means, by adopting this configuration, it is possible to prevent a trouble, such as leakage of the suspension K during transportation, in a reliable manner.

Also, according to the configuration in which the flat handle portion and the locking mechanism that allows the suspension storage container and the sample collecting member to engage with each other at a specific rotational position are provided, when the sample is collected, the user is able to pinch the flat handle portion between, for example, the first and second fingers. The portability of the sample collecting member can be therefore enhanced. Meanwhile, in a case where the handle portion and the suspension storage container are attached to each other through threaded engagement, they are locked at the position (threaded engagement operation completing position) at which their respective major axis directions are brought into agreement with each other by the locking mechanism. It is thus possible to make the feces collection container 1 compact after the sample is collected.

Also, when components in the sample are analyzed, it is general to set the feces collection container in the inspection system with the sealing film up. The holder is formed in the shape of a container having a hole formed along the outline of the feces collection container to open upward. It is thus possible to perform the work to insert the feces collection container into the holder quite easily when the feces collection container is locked at the threaded engagement operation completing position.

In the feces collection container described above, it is preferable that: the suspension storage container and the sample collecting member are provided with screw portions and the sample collecting member is attachable to the suspension storage container through threaded engagement of the both screw portions, and the sample bearing portion includes plural concave grooves formed on an outer peripheral surface at a tip end of the sample collecting member to align side by side in an axial direction; and the suspension storage container includes scraping claws allowed to be introduced into the respective concave grooves separately, and the scraping claws are successively introduced into the respective concave grooves in association with a relative translatory movement of the sample collecting member with respect to the suspension storage container by a tightening operation of the screw portions and scrape off the feces inside the concave grooves by undergoing relative displacement in a circumferential direction with respect to the concave grooves in association with a relative rotational movement of the sample collecting member with respect to the suspension storage container by the tightening operation for the feces to be dispersed in the suspension.

Meanwhile, according to the configuration in which the scraping claws and the concave grooves undergo relative displacement in response to a tightening operation of the both screw portions, the feces collected in the respective concave grooves can be scraped off inside the sample storage container in association with the threaded engagement of the both screw portions. It is thus possible to disperse the feces in the suspension in a reliable manner after the sample collecting member and the suspension storage container are attached to each other.

In the feces collection container described above, it is preferable that, of the chambers inside the suspension storage container, at least part of the chambers storing no suspension is filled with a cooling agent to cool the suspension.

According to the configuration in which, of the chambers inside the suspension storage container, the chambers storing no suspension are filled with a cooling agent, even in a case where the feces collection container is transported over a long period, the suspension can be maintained at a low temperature by means of the cooling agent. It is thus possible to prevent a change with time of the component to be inspected, such as hemoglobin, dispersed in the suspension, as much as possible while utilizing the chambers storing no suspension effectively.

According to the invention, it is possible to form a suspension storage container in a flat shape for the label to be laminated thereon with ease, and yet to achieve an enhancement of the strength in a direction orthogonal to the major axis direction of the flat cross section and a reduction of a necessary quantity of the suspension.

Also, according to the invention, because the sealing member is laminated to the tail end surfaces of the outer peripheral wall and the partition walls, in comparison with a case where the sealing member is laminated to the tail end surface of the outer peripheral wall alone, the lamination area for the sealing member can be increased, which can in turn enhance the lamination strength of the sealing member.

The invention claimed is:

1. A feces collection container including a suspension, a suspension storage container having an opening at a tip end and capable of storing the suspension inside thereof and a sample collecting member provided with a sample bearing portion at a tip end for a sample made of feces to adhere thereto and attachable to the suspension storage container at the opening at the tip end in a closely-attached state while the sample bearing portion is inserted into the suspension storage container, and configured in such a manner that the sample collecting member is attached to the suspension storage container while the sample bearing portion is dipped in the suspension, the feces collection container being characterized in that:

the suspension storage container has a flat portion across a specific region including a tail end;

the flat portion has an outer peripheral wall forming a flat outer peripheral surface and a partition wall extending in a flat cross section of the outer peripheral wall in a minor axis direction substantially orthogonal to a major axis direction of the flat cross section to partition a chamber inside the outer peripheral wall into plural chambers aligned side by side in the major axis direction, so that the suspension is stored only in part of the plural partitioned chambers, and that a sealing member having an outline almost identical with an outline of the outer peripheral wall is laminated on tail end surfaces of the outer peripheral wall and the partition wall;

the suspension storage container and the sample collecting member are provided with screw portions and the sample collecting member is attachable to the suspension storage container through threaded engagement of the screw portions, and the sample bearing portion includes plural concave grooves formed on an outer peripheral surface at a tip end of the sample collecting member to align side by side in an axial direction; and the suspension storage container includes a cylinder portion in proximity to the opening and dimensioned to remove extra feces adhering onto outer surface areas of the sample bearing portion as the sample bearing portion passes through the cylinder portion and scraping claws formed in positions to be soaked in the suspension when the suspension storage container opening faces up, the scraping claws being dimensioned and disposed to be introduced successively into the respective concave grooves in association with a translation of the sample collecting member with respect to the suspension storage container caused by a tightening of the screw portions so that the scraping claws scrape off the feces inside the concave grooves by undergoing relative displacement in a circumferential direction with respect to the concave grooves in association with a relative rotational movement of the sample collecting member with respect to the suspension storage container by the tightening operation for the feces to be dispersed in the suspension.

2. The feces collection container according to claim 1, wherein:

the flat portion has a pair of partition walls aligned side by side inside the outer peripheral wall in the major axis direction of the flat cross section, and the suspension is stored in a space between the partition walls.

3. The feces collection container according to claim 1, wherein:

the outer peripheral wall has a cross section almost in a shape of a rectangle, and the partition wall extends in a direction almost parallel to short sides of the rectangle.

4. The feces collection container according to claim 1, wherein:

the flat portion is formed almost across an entire area of the suspension storage container.

5. The feces collection container according to claim 1, wherein: the screw portion of the suspension storage container is formed at the opening at the tip end and the sample collecting member includes a flat handle portion formed at an end portion on an opposite side to the sample bearing portion and a screw portion formed between the handle portion and the sample bearing portion, and the feces collection container is configured in such a manner that the suspension storage container and the sample collecting member are attachable to each other through threaded engagement of the both screw portions;

the feces collection container includes a locking mechanism that allows the suspension storage container and the sample collecting member to engage with each other at a specific rotational position; and the locking mechanism defines a threaded engagement operation completing position at which a major axis direction of the handle portion and a major axis direction of the flat portion of the suspension storage container are brought almost into agreement with each other.

6. The feces collection container according to claim 1, wherein:

of the chambers inside the suspension storage container, at least part of the chambers storing no suspension is filled with a cooling agent to cool the suspension.

7. A feces collection container comprising:

a sample collecting member having a handle and a rod extending from the handle, outer peripheral portions of the rod remote from the handle having a plurality of concave grooves aligned side by side in an axial direction, and being configured for collecting a feces sample, threads between the handle and the concave grooves;

a suspension storage container having opposite first and second ends, an outer peripheral wall extending between the ends, first and second openings formed in the first and second ends respectively, at least part of the first opening defining a cylinder portion with threads configured for threadedly engaging the threads of the sample collecting member, the outer peripheral wall having opposite flat front and rear panels having a first width and opposite side panels extending between the front and rear panels and defining a second width less than the first width, at least one partition wall extending between the front and rear panels and dividing the suspension storage container into at least first and second chambers, the first chamber communicating with both the first and second openings and the second chamber spaced from the first and second openings, scraping claws formed in the first chamber and spaced from the threads of the cylinder portion by a distance substantially equal to the distance between the concave grooves and the threads of the sample collecting member; and a sealing film having an outline substantially identical to an outline of the peripheral wall of the suspension storage container and laminated to the outer peripheral wall and the partition wall at the second end of the storage container, the sealing film being pierceable by a nozzle for removing a suspension from the first chamber of the suspension storage container, whereby threaded engagement of the threads on the sample collecting member with the threads on the container causes the scraping claws to be introduced sequentially into the concave grooves of the sample collecting member and to move substantially circumferentially through the concave grooves for separating collected feces from the concave grooves.

8. The feces collecting container of claim 7, wherein the at least one partition wall comprises two partition walls dividing the suspension storage container into the first and second chambers and a third chamber.

9. The feces collecting container of claim 8, wherein the first chamber is between the second and third chambers.

10. The feces collecting container of claim 8, further comprising a label on the flat front panel.

11. The feces collection container of claim 10, wherein a distance between the front and rear panels is less than a distance between the partition walls.

12. The feces collection container of claim 11, wherein the second and third chambers are smaller than the first chamber.

13. The feces collecting container of claim 11, wherein the first chamber has a suspension therein and the second and third chamber have no suspension therein, the suspension being filled sufficiently in the first chamber to cover the scraping claws.

14. The feces collecting container of claim 7, further comprising a label on the flat front panel.

* * * * *